US008795738B2

(12) United States Patent
Yuan

(10) Patent No.: US 8,795,738 B2
(45) Date of Patent: Aug. 5, 2014

(54) USE OF ARSENIC FOR CANCER THERAPY PROTECTION

(75) Inventor: Zhi-Min Yuan, San Antonio, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 90 days.

(21) Appl. No.: 12/945,430

(22) Filed: Nov. 12, 2010

(65) Prior Publication Data

US 2011/0250291 A1    Oct. 13, 2011

Related U.S. Application Data

(60) Provisional application No. 61/260,662, filed on Nov. 12, 2009.

(51) Int. Cl.
*A61K 33/36* (2006.01)
*A61K 31/285* (2006.01)
*A61P 39/00* (2006.01)

(52) U.S. Cl.
USPC .......................... 424/620; 424/621; 514/504

(58) Field of Classification Search
USPC .................................. 424/620, 621; 514/504
See application file for complete search history.

(56) References Cited

U.S. PATENT DOCUMENTS

| 6,982,096 B2 | 1/2006 | Warrell, Jr. et al. |
| 7,521,071 B2 | 4/2009 | Kumana et al. |
| 2002/0001629 A1 | 1/2002 | Voellmy |
| 2009/0246291 A1 * | 10/2009 | Burger et al. ................. 424/623 |
| 2011/0250291 A1 | 10/2011 | Yuan |

FOREIGN PATENT DOCUMENTS

| KR | 10-2003-0058019 A | 7/2003 |
| WO | WO 2005065723 A1 * | 7/2005 |
| WO | WO 2009/120697 A2 | 10/2009 |
| WO | 2010071308 | 6/2010 |

OTHER PUBLICATIONS

Low Dose Arsenic Trioxide as a Potential Chemotherapy Protector, ClinicalTrials.gov (2012).*
Halasi et al., Celly Cycle (2009), vol. 8, No. 17, pp. 2850-2851.*
Kirsch et al., Science (2010), vol. 327, pp. 593-596.*
Karlsson et al., Clinical Cancer Research (2004), vol. 10, pp. 3179-3188.*
Park et al. "Tetra-arsenic oxide (Tetras) enhances radiation sensitivity of solid tumors by anti-vascular effect" Cancer Letters, 277 (2009), 212-217, May 2009.
Sui et al. "Arsenic trioxide enhances the therapeutic efficacy of adjuvant post-operative chemotherapy of gastric carcinoma while protecting bone marrow" Chinese-German Journal of Clinical Oncology Jul. 2009, vol. 8, No. 7, p. 406-p. 410.
Kumar et al. "Arsenic trioxide enhances the therapeutic efficacy of radiation treatment of oral squamous carcinoma while protecting bone" Mol. Cancer Ther. 2008;7(7), 2060-2069.
Huang et al. "Induction of Cytoplasmic Accumulation of p53: A Mechanism for Low Levels of Arsenic Exposure to Predispose Cells for Malignant Transformation" Cancer Res 2008; 68: (22), 9131-9136.
Burns et al. "Arsenic-Induced Enhancement of Ultraviolet Radiation Carcinogenesis in Mouse Skin: A Dose—Response Study" Environ. Health Perspect. 112:599-603 (2004).
Gurney "How to calculate the dose of chemotherapy" British Journal of Cancer (2002) 86, 1297-1302.
Botchkarev et al. "p53 is Essential for Chemotherapy-Induced Hair Loss" Cancer Res 60(18):5002-6 (2000).
Clarke. "Human Breast Cancer Cell Line Xenografts are Models of Breast Cancer—the Immunobiologies of Recipient Mice and the Characteristics of Several Tumorigenic Cell Lines" Breast Cancer Research and Treatment 39:69-86 (1996).
Dutkiewica "Experimental Studies on Arsenic Absorption Routes in Rats" Environmental Health Perspective 19:173-177 (1977).
Gudkov et al. "The Role of p53 in Determining Sensitivity to Radiation" Nature Reviews 3:117-129 (2003).
Inaba et al, "Evaluation of Antitumor Activity in a Human Breast Tumor/Nude Mouse Model with a Special Emphasis on Treatment Dose" Cancer 64:1577-1582 (1989).
Inoue et al. "Antitumor Efficacy of Seventeen Anticancer Drugs in Human Breast Cancer Xenograft (MX-1) Transplanted in Nude Mice" Cancer Chemother Pharmacol. 10(3):182-6 (1984).
Jonnalagadda et al. "Toxicity, Bioavailability and Metal Speciation" Comp Biochem Physiol 106C(3):585-595 (1993).
Kerbel. "Human Tumor Xenografts as Predictive Preclinical Models for Anticancer Drug Activity in Humans" Cancer Biology and Therapy 2:4:Suppl 1, 5134-5139 (2003).
Komarov et al. "A Chemical Inhibitor of p53 that Protects Mice from the Side Effects of Cancer Therapy" Science 285:1733-1737 (1999).
Komarova et al. "Chemoprotection from p53-Dependent Apoptosis: Potential Clinical Applications of the p53 Inhibitors" Biochem Pharmacol 62(6):657-667 (2001).
Lamm et al. "Arsenic in Drinking Water and Bladder Cancer Mortality in the United States: an Analysis Based on 133 U.S. Counties and 30 Years of Observation" J Occup Environ Med 46(3):298-306 (2004).
Powell et al. "Arsenic Trioxide Improves Event Free and Overall Survival for Adults with Acute Bromyelocytic Leukemia: North American Leukemia Intergroup Study C9710" Blood 116:3751-3757 (2010).
Trisonex™ (arsenic trioxide) injection label information) (2000).
Watanabe et al. "Metabolism of arsenic and its toxicological relevance" Arch Toxicol DOI 10.1007/s00204-012-0904-5 (2012).
Chiu, H-W. et al., "Combination treatment with arsenic trioxide and irradiation enhances cell-killing effects in human fibrosarcoma cells in vitro and in vivo through induction of both autophagy and apoptosis", Autophagy, Apr. 1, 2010, vol. 6, No. 3, pp. 353-365.
Park, J-H. et al., "Combination treatment with arsenic trioxide and sulindac enhances apoptotic cell death in lung cancer cells via activation of oxidative stress and mitogen-activated protein kinases", Oncology Reports, 2008, vol. 20, pp. 379-384.
International Search Report and Written Opinion issued in PCT Application No. PCT/US2012/037560, mailed Aug. 6, 2012 (12 pages).

* cited by examiner

Primary Examiner — Abigail Fisher
Assistant Examiner — Frank Choi
(74) Attorney, Agent, or Firm — Myers Bigel Sibley & Sajovec, PA

(57) ABSTRACT

A method of inhibiting damage to non-cancerous cells in a human subject during chemotherapeutic treatment or radiation treatment of cancer cells in the human subject includes administering to the human subject arsenic and/or one or more compounds of arsenic in a therapeutically effective amount prior to treatment with radiation or one or more chemotherapeutic agents.

8 Claims, 6 Drawing Sheets

USE OF ARSENIC FOR CANCER THERAPY PROTECTION

PRIORITY CLAIM

This application claims the benefit of U.S. Provisional Application No. 61/260,662 filed on Nov. 12, 2009.

STATEMENT REGARDING FEDERALLY SPONSORED RESEARCH OR DEVELOPMENT

This invention was made with government support under grant no. CA085679 awarded by the National Institutes of Health. The government has certain rights in the invention.

BACKGROUND OF THE INVENTION

1. Field of the Invention

The present invention relates generally to the treatment of cancer. The invention, more particularly is directed to the amelioration of side effects caused by chemo and radiation cancer therapies.

2. Description of the Relevant Art

Cancers are a leading cause of death in animals and humans. During the past decade, a combination of chemotherapy and radiation therapy along with surgery has become a standard approach for treatment of cancer patients in the curative as well as in the palliative setting. Though radiation and chemotherapy are successful modalities of cancer therapy, they do not greatly differentiate between cancerous and normal cells. Thus, in the process of killing cancer cells, radiation or chemotherapeutic agents also damage normal tissues leading to systemic toxicity and adverse side effects, which often poses a significant threat to cancer patients. Adverse side effects also greatly limit the maximum allowable dose. Efforts to avoid the toxicity of chemotherapy and radiation therapy have not yielded significant results despite multiple efforts in the past.

SUMMARY OF THE INVENTION

A method of inhibiting damage to non-cancerous cells in a human subject during chemotherapeutic treatment of cancer cells in the human subject includes administering to the human subject, in need of a chemotherapeutic treatment for the treatment of cancer, arsenic and/or one or more compounds of arsenic in a therapeutically effective amount. One or more chemotherapeutic agents are administered to the human subject subsequent to administration to arsenic and/or one or more compounds of arsenic. The arsenic and/or one or more compounds of arsenic are administered in an amount sufficient to inhibit damage to non-cancerous cells in the human subject when the chemotherapeutic agent is administered to the human subject.

In some embodiments, arsenic trioxide is administered to the human subject prior to administering the one or more chemotherapeutic agents to the human subject. In one embodiment, arsenic and/or one or more compounds of arsenic are administered to the human subject at least one day prior to administration of one or more chemotherapeutic agents to the human subject.

A method of inhibiting damage to non-cancerous cells in a human subject during radiation treatment of cancer cells in the human subject includes administering to the human subject, in need of a radiation treatment for the treatment of cancer, arsenic and/or one or more compounds of arsenic in a therapeutically effective amount. Radiation is administered to the human subject subsequent to administration of arsenic and/or one or more compounds of arsenic. The arsenic and/or one or more compounds of arsenic are administered in an amount sufficient to inhibit damage to non-cancerous cells in the human subject when the radiation is administered to the human subject.

In some embodiments, arsenic trioxide is administered to the human subject prior to administering the radiation treatment to the human subject. In one embodiment, arsenic and/or one or more compounds of arsenic are administered to the human subject at least one day prior to administration of the radiation treatment to the human subject.

A method of inhibiting side effects in a human subject during chemotherapeutic treatment of cancer cells in the human subject includes administering to the human subject, in need of a chemotherapeutic treatment for the treatment of cancer, arsenic and/or one or more compounds of arsenic in a therapeutically effective amount. One or more chemotherapeutic agents or radiation is administered to the human subject subsequent to administration of arsenic and/or one or more compounds of arsenic. The arsenic and/or one or more compounds of arsenic are administered in an amount sufficient to inhibit side effects caused by the chemotherapeutic or radiation treatment in the human subject when the chemotherapeutic agent is administered to the human subject.

Side effects that may be inhibited include side effects associated with the gastrointestinal system; side effects associated with low red blood cell count; side effects associated with low white blood cell count; side effects associated with low blood platelet count; side effects associated with depletion of bone marrow cells; side effects associated with cardiotoxicity; and side effects associated with loss of hair.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
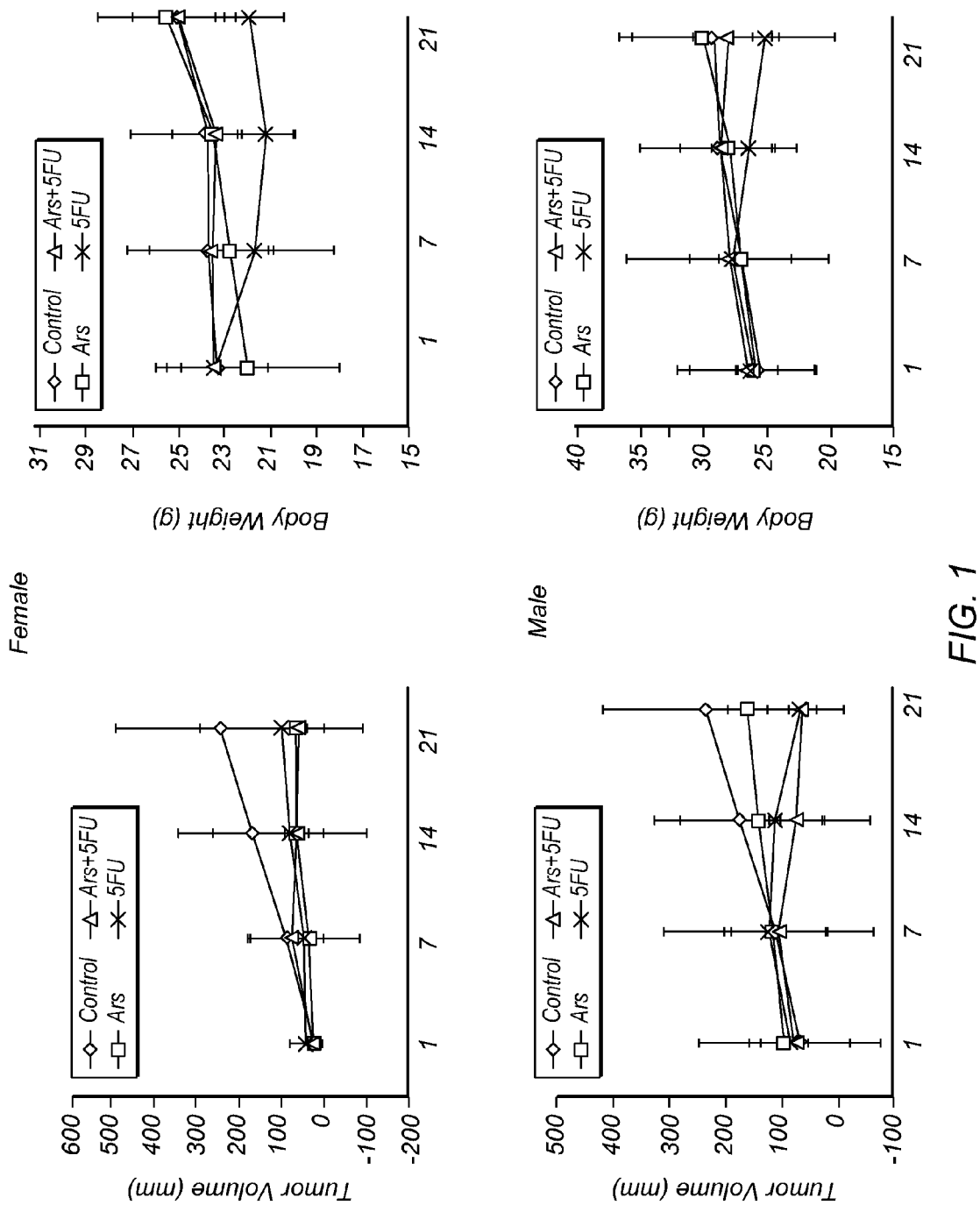
FIG. 1 depicts the effect of arsenic pretreatment on male mice injected with human lung carcinoma cells under various treatment conditions.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

The following definitions are provided:

As used herein the terms "administration," "administering," or the like, when used in the context of providing a composition to a subject generally refers to providing to the subject one or more pharmaceutical, "over-the-counter" (OTC) or nutraceutical compositions in combination with an appropriate delivery vehicle by any means such that the administered compound achieves one or more of the intended biological effects for which the compound was administered. By way of non-limiting example, a composition may be administered parenteral, subcutaneous, intravenous, intracoronary, rectal, intramuscular, intra-peritoneal, transdermal, or buccal routes of delivery. Alternatively, or concurrently, administration may be by the oral route. The dosage administered will be dependent upon the age, health, weight, and/or disease state of the recipient, kind of concurrent treatment, if any, frequency of treatment, and/or the nature of the effect desired. The dosage of pharmacologically active compound that is administered will be dependent upon multiple factors, such as the age, health, weight, and/or disease state of the recipient, concurrent treatments, if any, the frequency of treatment, and/or the nature and magnitude of the biological effect that is desired.

The term "cancer" as used herein is defined as a tissue of uncontrolled growth or proliferation of cells, such as a tumor. In a specific embodiment the tumor leads to local invasion and metastasis.

The term "chemotherapeutic agent" as used herein is defined as a drug, toxin, compound, composition or biological entity which is used as treatment for cancer.

The term "cytotoxic agent" as used herein is defined as a drug, toxin, compound, composition or biological entity which is used to kill a cell. In an embodiment the cell is a cancer cell.

The term "DNA-damaging agent" as used herein is a drug, toxin, compound, composition or biological entity which damages nucleic acid. The damage may be of any kind to the nucleic acid, for example, to break one or both strands of a DNA double helix molecule or to cause mutation of one or more nucleotides.

The term "drug" as used herein is defined as a medicament or medicine which is used for the therapeutic treatment of a medical condition or disease. The drug may be used in combination with another drug or type of therapy and in an embodiment is effective for the treatment of cancer.

The term "pharmaceutically or pharmacologically acceptable" as used herein refers to molecular entities and compositions that do not produce adverse, allergic, or other untoward reactions when administered to an animal or a human.

The term "pharmaceutically acceptable carrier" as used herein includes any and all solvents, dispersion media, coatings, antibacterial and antifungal agents, isotonic and absorption delaying agents and the like.

As used herein, terms such as "pharmaceutical composition," "pharmaceutical formulation," "pharmaceutical preparation," or the like, generally refer to formulations that are adapted to deliver a prescribed dosage of one or more pharmacologically active compounds to a cell, a group of cells, an organ or tissue, an animal or a human. Methods of incorporating pharmacologically active compounds into pharmaceutical preparations are widely known in the art. The determination of an appropriate prescribed dosage of a pharmacologically active compound to include in a pharmaceutical composition in order to achieve a desired biological outcome is within the skill level of an ordinary practitioner of the art. A pharmaceutical composition may be provided as sustained-release or timed-release formulations. Such formulations may release a bolus of a compound from the formulation at a desired time, or may ensure a relatively constant amount of the compound present in the dosage is released over a given period of time. Terms such as "sustained release," "controlled release," or "timed release" and the like are widely used in the pharmaceutical arts and are readily understood by a practitioner of ordinary skill in the art. Pharmaceutical preparations may be prepared as solids, semi-solids, gels, hydrogels, liquids, solutions, suspensions, emulsions, aerosols, powders, or combinations thereof. Included in a pharmaceutical preparation may be one or more carriers, preservatives, flavorings, excipients, coatings, stabilizers, binders, solvents and/or auxiliaries that are, typically, pharmacologically inert. It will be readily appreciated by an ordinary practitioner of the art that, included within the meaning of the term are pharmaceutically acceptable salts of compounds. It will further be appreciated by an ordinary practitioner of the art that the term also encompasses those pharmaceutical compositions that contain an admixture of two or more pharmacologically active compounds, such compounds being administered, for example, as a combination therapy.

As used herein the terms "subject" generally refers to a mammal, and in particular to a human.

The term "to treat" as used herein is defined as the practice of applying a treatment for a medical condition or disease. The treatment need not provide a complete cure and is considered effective if at least one symptom is improved upon or eradicated. Furthermore, the treatment need not provide a permanent improvement of the disease state or medical condition, although this is preferable.

The terms "in need of treatment," "in need thereof," "who would benefit from such treatment," or the like when used in the context of a subject being administered a pharmacologically active composition, generally refers to a judgment made by an appropriate healthcare provider that an individual or animal requires or will benefit from a specified treatment or medical intervention. Such judgments may be made based on a variety of factors that are in the realm of expertise of healthcare providers, but include knowledge that the individual or animal is ill, will be ill, or is at risk of becoming ill, as the result of a condition that may be ameliorated or treated with the specified medical intervention.

"Side effects" associated with chemotherapy or radiation therapy include, but are not limited to: abdominal pain, acid indigestion, acid reflux, alopecia (hair loss), anemia, poor appetite, early satiety, arthralgias (joint pain), asthenia, ataxia, azotemia, hepatotoxicity, bronchitis, constipation, cystitis, deep vein thrombosis (DVT), dyspepsia, dyspnea, edema, esophagitis, granulocytopenia, gynecomastia, hematoma, hemorrhagic cystitis, leukopenia, mucositis, myalgias, myocarditis, nephrotoxicity, neutropenia, pancytopenia, pericarditis, pharyngitis, stomatitis, thrombocytopenia, xerostomia, dry skin, flushing, hyperpigmentation, nail changes, photosensitivity, radiation recall, and rashes. In some embodiments, side effects include side effects due to neutropenia (a low white blood cell count). A low white blood cell count can lead to an increase in infections in the body. In some embodiments, side effects include side effects due to anemia (a low red blood cell count). A low red blood cell count can lead to side effects such as headaches and fatigue. In some embodiments, side effects include side effects due to thrombocytopenia (a low blood platelet count). A low blood platelet count can lead to side effects such as increased bruising, petechiae, and bleeding (e.g., nose, gums, rectal, etc.).

Other side effects include gastrointestinal side effects (e.g., nausea, abdominal pain, abdominal cramping, flatulence (gas), acid indigestion, acid reflux, poor appetite, early satiety, etc.). Other side effects include alopecia (hair loss) and skin reactions (e.g., dry skin, flushing, hyperpigmentation, nail changes, photosensitivity, radiation recall, and rashes).

The phrases "therapeutically effective amount" and "effective amount" are synonymous unless otherwise indicated, and mean an amount of a compound of the present invention that is sufficient to improve the condition, disease, or disorder being treated. Determination of a therapeutically effective amount, as well as other factors related to effective administration of a compound of the present invention to a patient in need of treatment, including dosage forms, routes of administration, and frequency of dosing, may depend upon the particulars of the condition that is encountered, including the patient and condition being treated, the severity of the condition in a particular patient, the particular compound being employed, the particular route of administration being employed, the frequency of dosing, and the particular formulation being employed. Determination of a therapeutically effective treatment regimen for a patient is within the level of ordinary skill in the medical or veterinarian arts. In clinical use, an effective amount may be the amount that is recommended by the U.S. Food and Drug Administration, or an equivalent foreign agency. The amount of active ingredient that can be combined with the carrier materials to produce a single dosage form varies depending upon the mammalian host treated and the particular mode of administration.

The term "tumor cell" as used herein is defined as a cell of a malignant mass, such as a tumor or cancer. The cell may be located within the tumor, on the surface of the tumor, or it may be associated with the tumor.

As used herein the terms "reducing," "inhibiting" and "ameliorating," when used in the context of modulating a pathological or disease state, generally refers to the prevention and/or reduction of at least a portion of the negative consequences of the disease state. When used in the context of a biochemical event or pathway, the term generally refers to a net reduction in the magnitude or activity of said pathway.

It is to be understood the present invention is not limited to particular chemotherapies or radiation therapies, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise.

In an embodiment, a method is provided in which the side effects of chemotherapy or radiation therapy in cancer patients are inhibited by administering arsenic and/or one or more compounds of arsenic to a patient, in conjunction with the administration of a chemotherapeutic agent and/or radiation to the patient. The arsenic and/or one or more compounds of arsenic are administered in an amount that is effective to reduce the side effects, but that is in an amount that is much less than an amount that will induce additional tumor formation. In some embodiments, arsenic and/or one or more compounds of arsenic are administered prior to the administration of chemotherapy or radiation therapy to the patient. In an embodiment, arsenic and/or one or more compounds of arsenic are administered substantially simultaneously, or after, the administration of chemotherapy or radiation therapy to the patient. Arsenic and/or one or more compounds of arsenic may be administered before; during and after chemotherapy or radiation therapy. The reduction in the severity of post-chemotherapy and post-radiation therapy side effects increases the quality of life experienced by patients receiving chemotherapy or radiotherapy. As an indication of such improved quality of life, the cancer patient is observed to have better appetite, better sleep, higher level of energy, less pain, less gastrointestinal problems, less hair loss, reduced incidence of infection, and desired weight gain, in comparison to patients that have not undergone a pretreatment with arsenic.

Arsenic and/or one or more compounds of arsenic may be administered prior to the treatment of a patient having cancer with radiation therapy or chemotherapy. In an embodiment, arsenic and/or one or more compounds of arsenic may be administered at least one day prior to treating the patient with radiation or one or more chemotherapeutic agents. In an embodiment, arsenic and/or one or more compounds of arsenic may be administered for a period of one, two or three consecutive days with the final dosage of the consecutively administered dosages being administered prior to treating the patient with radiation or one or more chemotherapeutic agents. Arsenic and/or one or more compounds of arsenic may be administered once a day, twice a day, three times a day, four times a day, six times a day, or substantially continuously (e.g., by intravenous administration).

The amount of arsenic and/or one or more compounds of arsenic added may be in an amount that is sufficient to protect non-cancerous cells from the effects of the radiation treatment without exhibiting significant toxicity to the human subject. In some embodiments an appropriate dosage of arsenic and/or one or more compounds of arsenic is in the range of 1-30 µg/kg, 2-20 µg/kg, or 5-10 µg/kg. The dosage of arsenic is given in an amount that is not generally sufficient to treat the cancer cells. For example, the dosage of arsenic is selected such that the arsenic and/or one or more compounds of arsenic provided have no substantial effect on the promotion or inhibition of tumor progression.

Examples of compounds of arsenic that may be used include, but are not limited to: arsenic (III) oxide ($As_2O_3$), arsenic (V) oxide ($As_2O_5$), arsenic (III) selenide ($As_2Se_3$), arsenic (II) sulfide ($As_2S_2$), arsenic (III) sulfide ($As_2S_3$), arsenic (V) sulfide ($As_2O_5$), arsenic (III) telluride ($As_2Te_3$), sodium arsenate ($Na_2HAsO_4$), potassium arsenate ($KH_2AsO_4$), sodium arsenyl tartrate ($NaC_4H_4AsO_6$) and other derivatives of arsenic.

Radiotherapeutic agents and factors include radiation and waves that induce DNA damage for example, gamma-irradiation, X-rays, UV-irradiation, microwaves, electronic emissions, radioisotopes, and the like. Therapy may be achieved by irradiating the localized tumor site with the above described forms of radiations. It is most likely that all of these factors effect a broad range of damage on: DNA; on the precursors of DNA; on the replication and repair ability of DNA, and on the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

Chemotherapeutic agents include agents that directly cross-link DNA, agents that intercalate into DNA, and agents that lead to chromosomal and mitotic aberrations by affecting nucleic acid synthesis. Examples of chemotherapeutic agents include, but are not limited to: doxorubicin, daunorubicin, mitomycin, actinomycin D, bleomycin, cisplatin, etoposide, tumor necrosis factor, taxol, vincristine, vinblastine, carmustine, melphalan, cyclophosphamide, chlorambucil, busulfan, fluorouracil ("5FU") and lomustine. Any of these agents may be used alone, or in combination with other agents, after pre-treatment of the patient with arsenic and/or one or more compounds of arsenic. The pretreatment of the patient with arsenic and/or one or more compounds of arsenic reduces the intensity and occurrence of many of the side effects of the above-listed chemotherapeutic agents without significantly inhibiting the efficacy of such agents.

Agents that directly cross-link nucleic acids, specifically DNA, are envisaged and are shown herein, to eventuate DNA damage leading to a synergistic antineoplastic combination. Agents such as cisplatin, and other DNA alkylating agents may be used.

Agents that damage DNA also include compounds that interfere with DNA replication, mitosis, and chromosomal segregation. Examples of these compounds include doxorubicin (also known as adriamycin), etoposide (also known as VP-16), verapamil, podophyllotoxin, and the like. Widely used in clinical setting for the treatment of neoplasms, these compounds are administered through bolus injections intravenously at doses ranging from 25-75 mg/m$^2$ at 21 day intervals for adriamycin, to 35-100 mg/m$^2$ for etoposide intravenously or orally.

Doxorubicin hydrochloride, 5,12-Naphthacenedione, (8s-cis)-10-((3-amino-2,3,6-trideoxy-a-L-lyxo-hexopyranosyl)oxy)-7,8,9,10-tetrahydro-6,8,11-trihydroxy-8-(hydroxyacetyl)-1-methoxy-hydrochloride (hydroxydaunorubicin hydrochloride, Adriamycin) is used in a wide antineoplastic spectrum. It binds to DNA and inhibits nucleic acid synthesis, inhibits mitosis and promotes chromosomal aberrations.

Administered alone, it is the drug of first choice for the treatment of thyroid adenoma and primary hepatocellular carcinoma. It is a component of 31 first-choice combinations for the treatment of ovarian, endometrial and breast tumors, bronchogenic oat-cell carcinoma, non-small cell lung carcinoma, gastric adenocarcinoma, retinoblastoma, neuroblastoma, mycosis fungoides, pancreatic carcinoma, prostatic carcinoma, bladder carcinoma, myeloma, diffuse histiocytic lymphoma, Wilms' tumor, Hodgkin's disease, adrenal tumors, osteogenic sarcoma soft tissue sarcoma, Ewing's sarcoma, rhabdomyosarcoma and acute lymphocytic leukemia. It is an alternative drug for the treatment of islet cell, cervical, testicular and adrenocortical cancers. It is also an immunosuppressant.

Doxorubicin is absorbed poorly and is typically administered intravenously. The pharmacokinetics are multicompartmental. Distribution phases have half-lives of 12 minutes and 3.3 hr. The elimination half-life is about 30 hr. Forty to 50% is secreted into the bile. Most of the remainder is metabolized in the liver, partly to an active metabolite (doxorubicinol), but a few percent is excreted into the urine. In the presence of liver impairment, the dose is typically inhibited.

Appropriate doses are, intravenous, adult, 60 to 75 mg/m$^2$ at 21-day intervals or 25 to 30 mg/m$^2$ on each of 2 or 3 successive days repeated at 3- or 4-wk intervals or 20 mg/m$^2$ once a week. The lowest dose should be used in elderly patients, when there is prior bone-marrow depression caused by prior chemotherapy or neoplastic marrow invasion, or when the drug is combined with other myelopoietic suppressant drugs. The dose should be reduced by 50% if the serum bilirubin lies between 1.2 and 3 mg/dL and by 75% if above 3 mg/dL. The lifetime total dose should not exceed 550 mg/m$^2$ in patients with normal heart function and 400 mg/m$^2$ in persons having received mediastinal irradiation. Alternatively, 30 mg/m$^2$ on each of 3 consecutive days, repeated every 4 wk. Exemplary doses may be 10 mg/m$^2$, 20 mg/m$^2$, 30 mg/m$^2$, 50 mg/m$^2$, 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

Daunorubicin hydrochloride, 5,12-Naphthacenedione, (8S-cis)-8-acetyl-10-((3-amino-2,3,6-trideoxy-a-L-lyxo-hexanopyranosyl)oxy)-7,8,9,10-tetrahydro-6,8,11-trihydroxy-10-methoxy hydrochloride; also known as cerubidine, is commercially available from Wyeth. Daunorubicin intercalates into DNA, blocks DNA-directed RNA polymerase and inhibits DNA synthesis. It can prevent cell division in doses that do not interfere with nucleic acid synthesis.

In combination with other drugs it is included in the first-choice chemotherapy of acute myelocytic leukemia in adults (for induction of remission), acute lymphocytic leukemia and the acute phase of chronic myelocytic leukemia. Oral absorption is poor, and it must be given intravenously. The half-life of distribution is 45 minutes and of elimination, about 19 hr. The half-life of its active metabolite, daunorubicinol, is about 27 hr. Daunorubicin is metabolized mostly in the liver and also secreted into the bile (ca 40%). Dosage must be reduced in liver or renal insufficiencies.

Suitable doses are (base equivalent), intravenous adult, younger than 60 yr. 45 mg/m$^2$/day (30 mg/m$^2$ for patients older than 60 yr.) for 1, 2 or 3 days every 3 or 4 wk or 0.8 mg/kg/day for 3 to 6 days every 3 or 4 wk; no more than 550 mg/m$^2$ should be given in a lifetime, except only 450 mg/m$^2$ if there has been chest irradiation; children, 25 mg/m$^2$ once a week unless the age is less than 2 yr. or the body surface less than 0.5 m, in which case the weight-based adult schedule is used. It is available in injectable dosage forms (base equivalent) 20 mg (as the base equivalent to 21.4 mg of the hydrochloride). Exemplary doses may be 10 mg/m$^2$, 20 mg/m$^2$, 30 mg/m$^2$, 50 mg/m$^2$, 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course these dosages are exemplary, and any dosage in-between these points is also expected to be of use in the invention.

Mitomycin (also known as mutamycin and/or mitomycin-C) is an antibiotic isolated from the broth of *Streptomyces caespitosus* which has been shown to have antitumor activity. The compound is heat stable, has a high melting point, and is freely soluble in organic solvents.

Mitomycin selectively inhibits the synthesis of deoxyribonucleic acid (DNA). The guanine and cytosine content correlates with the degree of mitomycin-induced cross-linking. At high concentrations of the drug, cellular RNA and protein synthesis are also suppressed.

In humans, mitomycin is rapidly cleared from the serum after intravenous administration. Time required to reduce the serum concentration by 50% after a 30 mg bolus injection is 17 minutes. After injection of 30 mg., 20 mg., or 10 mg. I.V., the maximal serum concentrations were 2.4 mg./mL, 1.7 mg./mL, and 0.52 mg./mL, respectively. Clearance is effected primarily by metabolism in the liver, but metabolism occurs in other tissues as well. The rate of clearance is inversely proportional to the maximal serum concentration because, it is thought, of saturation of the degradative pathways.

Approximately 10% of a dose of mitomycin is excreted unchanged in the urine. Since metabolic pathways are saturated at relatively low doses, the percent of a dose excreted in urine increases with increasing dose. In children, excretion of intravenously administered mitomycin is similar.

Actinomycin D (Dactinomycin) (50-76-0); $C_{62}H_{86}N_{12}O_{16}$ (1255.43) is an antineoplastic drug that inhibits DNA-dependent RNA polymerase. It is a component of first-choice combinations for treatment of choriocarcinoma, embryonal rhabdomyosarcoma, testicular tumor and Wilms' tumor. Tumors which fail to respond to systemic treatment sometimes respond to local perfusion. Dactinomycin potentiates radiotherapy. It is a secondary (efferent) immunosuppressive.

Actinomycin D is used in combination with primary surgery, radiotherapy, and other drugs, particularly vincristine and cyclophosphamide. Antineoplastic activity has also been noted in Ewing's tumor, Kaposi's sarcoma, and soft-tissue sarcomas. Actinomycin D can be effective in women with advanced cases of choriocarcinoma. It also produces consistent responses in combination with chlorambucil and methotrexate in patients with metastatic testicular carcinomas. A response may sometimes be observed in patients with Hodgkin's disease and non-Hodgkin's lymphomas. Actinomycin D has also been used to inhibit immunological responses, particularly the rejection of renal transplants.

Half of the dose is excreted intact into the bile and 10% into the urine; the half-life is about 36 hr. The drug does not pass the blood-brain barrier. Actinomycin D is supplied as a lyophilized powder (0/5 mg in each vial). The usual daily dose is 10 to 15 mg/kg; this is given intravenously for 5 days; if no manifestations of toxicity are encountered, additional courses may be given at intervals of 3 to 4 weeks. Daily injections of 100 to 400 mg have been given to children for 10 to 14 days; in other regimens, 3 to 6 mg/kg, for a total of 125 mg/kg, and weekly maintenance doses of 7.5 mg/kg have been used. Although it is safer to administer the drug into the tubing of an intravenous infusion, direct intravenous injections have been given, with the precaution of discarding the needle used to withdraw the drug from the vial in order to avoid subcutaneous reaction. Exemplary doses may be 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

Bleomycin is a mixture of cytotoxic glycopeptide antibiotics isolated from a strain of *Streptomyces verticillus*. It is freely soluble in water.

Although the exact mechanism of action of bleomycin is unknown, available evidence would seem to indicate that the main mode of action is the inhibition of DNA synthesis with some evidence of lesser inhibition of RNA and protein synthesis.

In mice, high concentrations of bleomycin are found in the skin, lungs, kidneys, peritoneum, and lymphatics. Tumor cells of the skin and lungs have been found to have high concentrations of bleomycin in contrast to the low concentrations found in hematopoietic tissue. The low concentrations of bleomycin found in bone marrow may be related to high levels of bleomycin degradative enzymes found in that tissue.

In patients with a creatinine clearance of >35 mL per minute, the serum or plasma terminal elimination half-life of bleomycin is approximately 115 minutes. In patients with a creatinine clearance of <35 mL per minute, the plasma or serum terminal elimination half-life increases exponentially as the creatinine clearance decreases. In humans, 60% to 70% of an administered dose is recovered in the urine as active bleomycin.

Bleomycin should be considered a palliative treatment. It has been shown to be useful in the management of the following neoplasms either as a single agent or in proven combinations with other approved chemotherapeutic agents in squamous cell carcinoma such as head and neck (including mouth, tongue, tonsil, nasopharynx, oropharynx, sinus, palate, lip, buccal mucosa, gingiva, epiglottis, larynx), skin, penis, cervix, and vulva. It has also been used in the treatment of lymphomas and testicular carcinoma.

Because of the possibility of an anaphylactoid reaction, lymphoma patients should be treated with two units or less for the first two doses. If no acute reaction occurs, then the regular dosage schedule may be followed.

Improvement of Hodgkin's Disease and testicular tumors is prompt and noted within 2 weeks. If no improvement is seen by this time, improvement is unlikely. Squamous cell cancers respond more slowly, sometimes requiring as long as 3 weeks before any improvement is noted.

Bleomycin may be given by the intramuscular, intravenous, or subcutaneous routes.

Cisplatin has been widely used to treat cancers such as metastatic testicular or ovarian carcinoma, advanced bladder cancer, head or neck cancer, cervical cancer, lung cancer or other tumors. Cisplatin can be used alone or in combination with other agents, with efficacious doses used in clinical applications of 15-20 mg/m$^2$ for 5 days every three weeks for a total of three courses. Exemplary doses may be 0.50 mg/m$^2$, 1.0 mg/m$^2$, 1.50 mg/m$^2$, 1.75 mg/m$^2$, 2.0 mg/m$^2$, 3.0 mg/m$^2$, 4.0 mg/m$^2$, 5.0 mg/m$^2$, 10 mg//m$^2$ Of course, all of these dosages are exemplary, and any dosage in-between these points is also expected to be of use in the invention.

Cisplatin is not absorbed orally and must therefore be delivered via injection intravenously, subcutaneously, intratumorally or intraperitoneally.

In certain aspects of the current invention cisplatin is used in combination with emodin or emodin-like compounds in the treatment of non-small cell lung carcinoma. It is clear, however, that the combination of cisplatin and emodin and or emodin-like compounds could be used for the treatment of any other neu-mediated cancer.

Etoposide is also know as VP16 and is used primarily for treatment of testicular tumors, in combination with bleomycin and cisplatin, and in combination with cisplatin for small-cell carcinoma of the lung. It is also active against non-Hodgkin's lymphomas, acute nonlymphocytic leukemia, carcinoma of the breast, and Kaposi's sarcoma associated with acquired immunodeficiency syndrome (AIDS).

Etoposide is available as a solution (20 mg/ml) for intravenous administration and as 50-mg, liquid-filled capsules for oral use. For small-cell carcinoma of the lung, the intravenous dose (in combination therapy) is can be as much as 100 mg/m$^2$ or as little as 2 mg/m$^2$, routinely 35 mg/m$^2$, daily for 4 days, to 50 mg/m$^2$, daily for 5 days have also been used. When given orally, the dose should be doubled. Hence the doses for small cell lung carcinoma may be as high as 200-250 mg/m$^2$. The intravenous dose for testicular cancer (in combination therapy) is 50 to 100 mg/m$^2$ daily for 5 days, or 100 mg/m$^2$ on alternate days, for three doses. Cycles of therapy are usually repeated every 3 to 4 weeks. The drug should be administered slowly during a 30- to 60-minute infusion in order to avoid hypotension and bronchospasm, which are probably due to the solvents used in the formulation.

Tumor Necrosis Factor (TNF; Cachectin) is a glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. Some infectious agents cause tumor regression through the stimulation of TNF production. TNF can be quite toxic when used alone in effective doses, so that the optimal regimens probably will use it in lower doses in combination with other drugs. Its immunosuppressive actions are potentiated by γ-interferon, so that the combination potentially is dangerous. A hybrid of TNF and interferon-α also has been found to possess anti-cancer activity.

Figure 6:
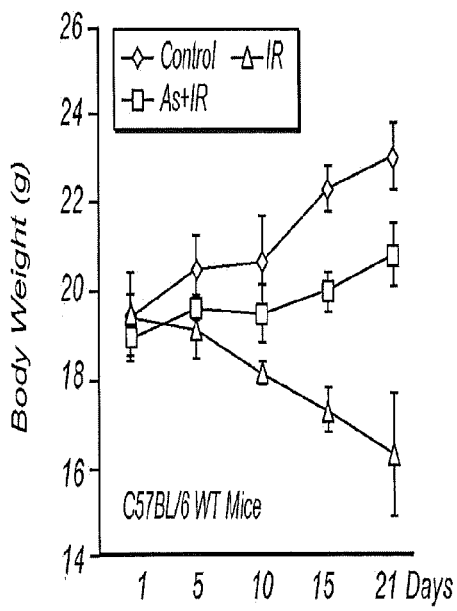
Figure 6:
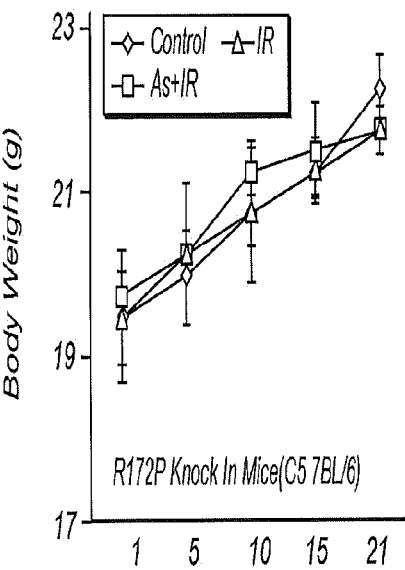
Figure 6:
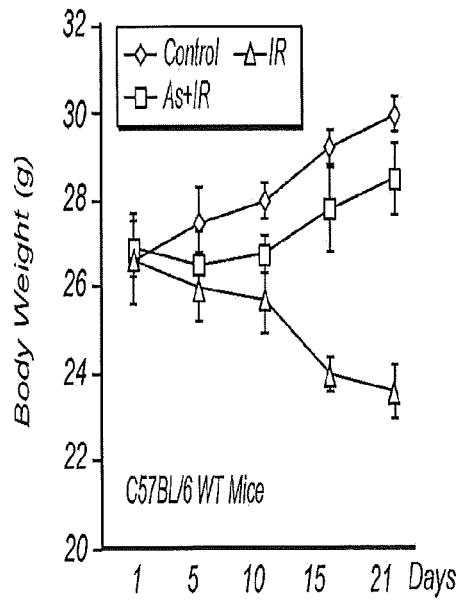
Figure 6:
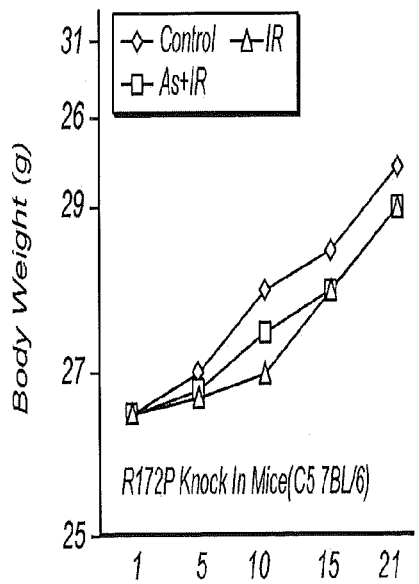

Taxol is an experimental antimitotic agent, isolated from the bark of the ash tree, *Taxus brevifolia*. It binds to tubulin (at a site distinct from that used by the vinca alkaloids) and promotes the assembly of microtubules. Taxol is currently being evaluated clinically; it has activity against malignant melanoma and carcinoma of the ovary. Maximal doses are 30 mg/m$^2$ per day for 5 days or 210 to 250 mg/m$^2$ given once every 3 weeks. Of course, all of these dosages are exemplary, and any dosage in-between these points is also expected to be of use in the invention. FIG. 6 is the illustration showing the conjugation of peptide with liposome carrying anti-cancer agent taxol through polyethylene glycol adapters.

Vincristine blocks mitosis and produces metaphase arrest. It seems likely that most of the biological activities of this drug can be explained by its ability to bind specifically to tubulin and to block the ability of protein to polymerize into microtubules. Through disruption of the microtubules of the mitotic apparatus, cell division is arrested in metaphase. The inability to segregate chromosomes correctly during mitosis presumably leads to cell death.

The relatively low toxicity of vincristine for normal marrow cells and epithelial cells make this agent unusual among anti-neoplastic drugs, and it is often included in combination with other myelosuppressive agents.

Unpredictable absorption has been reported after oral administration of vinblastine or vincristine. At the usual clinical doses the peak concentration of each drug in plasma is approximately 0.4 mM.

Vinblastine and vincristine bind to plasma proteins. They are extensively concentrated in platelets and to a lesser extent in leukocytes and erythrocytes.

Vincristine has a multiphasic pattern of clearance from the plasma; the terminal half-life is about 24 hours. The drug is metabolized in the liver, but no biologically active derivatives have been identified. Doses should be reduced in patients with hepatic dysfunction. At least a 50% reduction in dosage is indicated if the concentration of bilirubin in plasma is greater than 3 mg/dl (about 50 mM).

Vincristine sulfate is available as a solution (1 mg/ml) for intravenous injection. Vincristine used together with corticosteroids is presently the treatment of choice to induce remissions in childhood leukemia; the optimal dosages for these drugs appear to be vincristine, intravenously, 2 mg/m$^2$ of body-surface area, weekly, and prednisolone, orally, 40 mg/m$^2$, daily. Adult patients with Hodgkin's disease or non-Hodgkin's lymphomas usually receive vincristine as a part of a complex protocol. When used in the MOPP regimen, the recommended dose of vincristine is 1.4 mg/m$^2$. High doses of vincristine seem to be tolerated better by children with leukemia than by adults, who may experience sever neurological toxicity. Administration of the drug more frequently than every 7 days or at higher doses seems to increase the toxic manifestations without proportional improvement in the response rate. Precautions should also be used to avoid extravasation during intravenous administration of vincristine. Vincristine (and vinblastine) can be infused into the arterial blood supply of tumors in doses several times larger than those that can be administered intravenously with comparable toxicity.

Vincristine has been effective in Hodgkin's disease and other lymphomas. Although it appears to be somewhat less beneficial than vinblastine when used alone in Hodgkin's disease, when used with mechlorethamine, prednisolone, and procarbazine (the so-called MOPP regimen), it is the preferred treatment for the advanced stages (III and IV) of this disease. In non-Hodgkin's lymphomas, vincristine is an important agent, particularly when used with cyclophosphamide, bleomycin, doxorubicin, and prednisolone. Vincristine is more useful than vinblastine in lymphocytic leukemia. Beneficial response have been reported in patients with a variety of other neoplasms, particularly Wilms' tumor, neuroblastoma, brain tumors, rhabdomyosarcoma, and carcinomas of the breast, bladder, and the male and female reproductive systems.

Doses of vincristine for use will be determined by the clinician according to the individual patients need. 0.01 to 0.03 mg/kg or 0.4 to 1.4 mg/m$^2$ can be administered or 1.5 to 2 mg/m$^2$ can also be administered. Alternatively 0.02 mg/m$^2$, 0.05 mg/m$^2$, 0.06 mg/m$^2$, 0.07 mg/m$^2$, 0.08 mg/m$^2$, 0.1 mg/m$^2$, 0.12 mg/m$^2$, 0.14 mg/m$^2$, 0.15 mg/m$^2$, 0.2 mg/m$^2$, 0.25 mg/m$^2$ can be given as a constant intravenous infusion. Of course, all of these dosages are exemplary, and any dosage in-between these points is also expected to be of use in the invention.

When cells are incubated with vinblastine, dissolution of the microtubules occurs. Unpredictable absorption has been reported after oral administration of vinblastine or vincristine. At the usual clinical doses the peak concentration of each drug in plasma is approximately 0.4 mM. Vinblastine and vincristine bind to plasma proteins. They are extensively concentrated in platelets and to a lesser extent in leukocytes and erythrocytes.

After intravenous injection, vinblastine has a multiphasic pattern of clearance from the plasma; after distribution, drug disappears from plasma with half-lives of approximately 1 and 20 hours.

Vinblastine is metabolized in the liver to biologically activate derivative desacetylvinblastine. Approximately 15% of an administered dose is detected intact in the urine, and about 10% is recovered in the feces after biliary excretion. Doses should be reduced in patients with hepatic dysfunction. At least a 50% reduction in dosage is indicated if the concentration of bilirubin in plasma is greater than 3 mg/dl (about 50 mM).

Vinblastine sulfate is available in preparations for injection. The drug is given intravenously; special precautions must be taken against subcutaneous extravasation, since this may cause painful irritation and ulceration. The drug should not be injected into an extremity with impaired circulation. After a single dose of 0.3 mg/kg of body weight, myelosuppression reaches its maximum in 7 to 10 days. If a moderate level of leukopenia (approximately 3000 cells/mm$^3$) is not attained, the weekly dose may be increased gradually by increments of 0.05 mg/kg of body weight. In regimens designed to cure testicular cancer, vinblastine is used in doses of 0.3 mg/kg every 3 weeks irrespective of blood cell counts or toxicity.

The most important clinical use of vinblastine is with bleomycin and cisplatin in the curative therapy of metastatic testicular tumors. Beneficial responses have been reported in various lymphomas, particularly Hodgkin's disease, where significant improvement may be noted in 50 to 90% of cases. The effectiveness of vinblastine in a high proportion of lymphomas is not diminished when the disease is refractory to alkylating agents. It is also active in Kaposi's sarcoma, neuroblastoma, and Letterer-Siwe disease (histiocytosis X), as well as in carcinoma of the breast and choriocarcinoma in women.

Doses of vinblastine for use will be determined by the clinician according to the individual patients need. 0.1 to 0.3 mg/kg can be administered or 1.5 to 2 mg/m$^2$ can also be administered. Alternatively, 0.1 mg/m$^2$, 0.12 mg/m$^2$, 0.14 mg/m$^2$, 0.15 mg/m$^2$, 0.2 mg/m$^2$, 0.25 mg/m$^2$, 0.5 mg/m$^2$, 1.0 mg/m$^2$, 1.2 mg/m$^2$, 1.4 mg/m$^2$, 1.5 mg/m$^2$, 2.0 mg/m$^2$, 2.5 mg/m$^2$, 5.0 mg/m$^2$, 6 mg/m$^2$, 8 mg/m$^2$, 9 mg/m$^2$, 10 mg/m$^2$, 20 mg/m$^2$, can be given. Of course, all of these dosages are exemplary, and any dosage in-between these points is also expected to be of use in the invention.

Carmustine (sterile carmustine) is one of the nitrosoureas used in the treatment of certain neoplastic diseases. It is 1,3bis(2-chloroethyl)-1-nitrosourea. It is lyophilized pale yellow flakes or congealed mass with a molecular weight of 214.06. It is highly soluble in alcohol and lipids, and poorly soluble in water. Carmustine is administered by intravenous infusion after reconstitution as recommended. Sterile carmustine is commonly available in 100 mg single dose vials of lyophilized material.

Although it is generally agreed that carmustine alkylates DNA and RNA, it is not cross resistant with other alkylators. As with other nitrosoureas, it may also inhibit several key enzymatic processes by carbamoylation of amino acids in proteins.

Carmustine is indicated as palliative therapy as a single agent or in established combination therapy with other approved chemotherapeutic agents in brain tumors such as glioblastoma, brainstem glioma, medulloblardyoma, astrocytoma, ependymoma, and metastatic brain tumors. Also it has been used in combination with prednisolone to treat multiple myeloma. Carmustine has proved useful, in the treatment of Hodgkin's Disease and in non-Hodgkin's lymphomas, as secondary therapy in combination with other approved drugs in patients who relapse while being treated with primary therapy, or who fail to respond to primary therapy.

The recommended dose of carmustine as a single agent in previously untreated patients is 150 to 200 mg/m$^2$ intravenously every 6 weeks. This may be given as a single dose or divided into daily injections such as 75 to 100 mg/m$^2$ on 2 successive days. When carmustine is used in combination with other myelosuppressive drugs or in patients in whom bone marrow reserve is depleted, the doses should be adjusted accordingly. Doses subsequent to the initial dose should be adjusted according to the hematologic response of the patient to the preceding dose. It is of course understood that other doses may be used in the present invention for example 10 mg/m$^2$, 20 mg/m$^2$, 30 mg/m$^2$, 40 mg/m$^2$, 50 mg/m$^2$, 60 mg/m$^2$, 70 mg/m$^2$, 80 mg/m$^2$, 90 mg/m$^2$, 100 mg/m$^2$. The skilled artisan is directed to, "Remington's Pharmaceutical Sciences" 15th Edition, chapter 61. Some variation in dosage will necessarily occur depending on the condition of the subject being treated. The person responsible for administration will, in any event, determine the appropriate dose for the individual subject Melphalan also known as alkeran, L-phenylalanine mustard, phenylalanine mustard, L-PAM, or L-sarcolysin, is a phenylalanine derivative of nitrogen mustard. Melphalan is a bifunctional alkylating agent which is active against selective human neoplastic diseases. It is known chemically as 4-(bis (2-chloroethyl)amino)-L-phenylalanine.

Melphalan is the active L-isomer of the compound and was first synthesized in 1953 by Bergel and Stock; the D-isomer, known as medphalan, is less active against certain animal tumors, and the dose needed to produce effects on chromosomes is larger than that required with the L-isomer. The racemic (DL-) form is known as merphalan or sarcolysin. Melphalan is insoluble in water and has a pKa$_1$ of .about.2.1. Melphalan is available in tablet form for oral administration and has been used to treat multiple myeloma.

Available evidence suggests that about one third to one half of the patients with multiple myeloma show a favorable response to oral administration of the drug.

Melphalan has been used in the treatment of epithelial ovarian carcinoma. One commonly employed regimen for the treatment of ovarian carcinoma has been to administer melphalan at a dose of 0.2 mg/kg daily for five days as a single course. Courses are repeated every four to five weeks depending upon hematologic tolerance. Alternatively the dose of melphalan used could be as low as 0.05 mg/kg/day or as high as 3 mg/kg/day or any dose in between these doses or above these doses. Some variation in dosage will necessarily occur depending on the condition of the subject being treated. The person responsible for administration will, in any event, determine the appropriate dose for the individual subject.

Cyclophosphamide is 2H-1,3,2-Oxazaphosphorin-2-amine, N,N-bis(2-chloroethyl)tetrahydro-, 2-oxide, monohydrate; termed Cytoxan available from Mead Johnson; and Neosar available from Adria. Cyclophosphamide is prepared by condensing 3-amino-1-propanol with N,N-bis(2-chlorethyl)phosphoramidic dichloride ((ClCH$_2$CH$_2$).sub.2 N—POCl$_2$) in dioxane solution under the catalytic influence of triethylamine. The condensation is double, involving both the hydroxyl and the amino groups, thus effecting the cyclization.

Unlike other β-chloroethylamino alkylators, it does not cyclize readily to the active ethyleneimonium form until activated by hepatic enzymes. Thus, the substance is stable in the gastrointestinal tract, tolerated well and effective by the oral and parental routes and does not cause local vesication, necrosis, phlebitis or even pain.

Suitable doses for adults include, orally, 1 to 5 mg/kg/day (usually in combination), depending upon gastrointestinal tolerance; or 1 to 2 mg/kg/day; intravenously, initially 40 to 50 mg/kg in divided doses over a period of 2 to 5 days or 10 to 15 mg/kg every 7 to 10 days or 3 to 5 mg/kg twice a week or 1.5 to 3 mg/kg/day. A dose 250 mg/kg/day may be administered as an antineoplastic. Because of gastrointestinal adverse effects, the intravenous route is preferred for loading. During maintenance, a leukocyte count of 3000 to 4000/mm$^3$ usually is desired. The drug also sometimes is administered intramuscularly, by infiltration or into body cavities. It is available in dosage forms for injection of 100, 200 and 500 mg, and tablets of 25 and 50 mg the skilled artisan is referred to "Remington's Pharmaceutical Sciences" 15th Edition, chapter 61, incorporate herein as a reference, for details on doses for administration.

Chlorambucil (also known as leukeran) is a bifunctional alkylating agent of the nitrogen mustard type that has been found active against selected human neoplastic diseases. Chlorambucil is known chemically as 4-(bis(2-chlorethyl) amino)benzenebutanoic acid.

Chlorambucil is available in tablet form for oral administration. It is rapidly and completely absorbed from the gastrointestinal tract. After single oral doses of 0.6-1.2 mg/kg, peak plasma chlorambucil levels are reached within one hour and the terminal half-life of the parent drug is estimated at 1.5 hours. 0.1 to 0.2 mg/kg/day or 3 to 6 mg/m$^2$/day or alternatively 0.4 mg/kg may be used for antineoplastic treatment. Treatment regimes are well know to those of skill in the art and can be found in the "Physicians Desk Reference" and in "Remington's Pharmaceutical Sciences" referenced herein.

Chlorambucil is indicated in the treatment of chronic lymphatic (lymphocytic) leukemia, malignant lymphomas including lymphosarcoma, giant follicular lymphoma and Hodgkin's disease. It is not curative in any of these disorders but may produce clinically useful palliation.

Busulfan (also known as myleran) is a bifunctional alkylating agent. Busulfan is known chemically as 1,4-butanediol dimethanesulfonate.

Busulfan is not a structural analog of the nitrogen mustards. Busulfan is available in tablet form for oral administration. Each scored tablet contains 2 mg busulfan and the inactive ingredients magnesium stearate and sodium chloride.

Busulfan is indicated for the palliative treatment of chronic myelogenous (myeloid, myelocytic, granulocytic) leukemia. Although not curative, busulfan reduces the total granulocyte mass, relieves symptoms of the disease, and improves the clinical state of the patient. Approximately 90% of adults with previously untreated chronic myelogenous leukemia will obtain hematologic remission with regression or stabilization of organomegaly following the use of busulfan. It has been shown to be superior to splenic irradiation with respect to survival times and maintenance of hemoglobin levels, and to be equivalent to irradiation at controlling splenomegaly.

Fluorouracil ("5FU") (sold under the brand names Adrucil, Carac, Efudex and Fluoroplex) is a drug that is a pyrimidine analog which is used in the treatment of cancer. Some of its principal uses are in colorectal cancer, and pancreatic cancer. It is also sometimes used in the treatment of inflammatory breast cancer.

Lomustine is one of the nitrosoureas used in the treatment of certain neoplastic diseases. It is 1-(2-chloro-ethyl)-3-cyclohexyl-1nitrosourea. It is a yellow powder with the empirical formula of $C_9H_{16}ClN_3O_2$ and a molecular weight of 233.71. Lomustine is soluble in 10% ethanol (0.05 mg per mL) and in absolute alcohol (70 mg per mL). Lomustine is relatively insoluble in water (<0.05 mg per mL). It is relatively unionized at a physiological pH. Inactive ingredients in lomustine capsules are: magnesium stearate and mannitol.

Although it is generally agreed that lomustine alkylates DNA and RNA, it is not cross resistant with other alkylators. As with other nitrosoureas, it may also inhibit several key enzymatic processes by carbamoylation of amino acids in proteins.

Lomustine may be given orally. Following oral administration of radioactive lomustine at doses ranging from 30 $mg/m^2$ to 100 $mg/m^2$, about half of the radioactivity given was excreted in the form of degradation products within 24 hours.

The serum half-life of the metabolites ranges from 16 hours to 2 days. Tissue levels are comparable to plasma levels at 15 minutes after intravenous administration.

Lomustine has been shown to be useful as a single agent in addition to other treatment modalities, or in established combination therapy with other approved chemotherapeutic agents in both primary and metastatic brain tumors, in patients who have already received appropriate surgical and/or radiotherapeutic procedures. It has also proved effective in secondary therapy against Hodgkin's Disease in combination with other approved drugs in patients who relapse while being treated with primary therapy, or who fail to respond to primary therapy.

The recommended dose of lomustine in adults and children as a single agent in previously untreated patients is 130 $mg/m^2$ as a single oral dose every 6 weeks. In individuals with compromised bone marrow function, the dose should be reduced to 100 $mg/m^2$ every 6 weeks. When lomustine is used in combination with other myelosuppressive drugs, the doses should be adjusted accordingly. It is understood that other doses may be used for example, 20 $mg/m^2$, 30 $mg/m^2$, 40 $mg/m^2$, 50 $mg/m^2$, 60 $mg/m^2$, 70 $mg/m^2$, 80 $mg/m^2$, 90 $mg/m^2$, 100 $mg/m^2$, 120 $mg/m^2$ or any doses between these figures as determined by the clinician to be necessary for the individual being treated.

Surgical treatment for removal of the cancerous growth is another standard procedure for the treatment of tumors and cancers. This attempts to remove the entire cancerous growth. However, surgery is generally combined with chemotherapy and/or radiotherapy to ensure the destruction of any remaining neoplastic or malignant cells. Thus, surgery may be used in addition to using radiation therapy and chemotherapy to treat tumors.

Induction of DNA damage is the principal mode of action for both radio- and chemotherapies to kill cancer cells, which also potently activates p53. Abundant evidence indicates that DNA damaging anticancer therapy-induced acute toxicity is mainly mediated by p53, which, upon activation, induces massive apoptotic cell death in sensitive tissues, including intestinal epithelium, spleen, bone marrow, thymus, tongue, testis and hair follicles, leading to severe pathological consequences. In line with these observations is the finding that cells with defective p53 are resistant to DNA damage-induced apoptosis. Moreover, genetic studies have shown that p53-deficient mice are refractory to toxicity induced by radiation and chemotherapy. The p53-mediated pathological response to chemotherapy and radiation therapy would suggest that suppression of p53 may serve as a potential approach for amelioration of the adverse side effects, allowing patients to tolerate much more aggressive (and so potentially more successful) treatment regimes. However, p53 is one of the most important tumor suppressors, so the potential cancer risk resulting from its inhibition needs to be addressed.

The p53 tumor suppressor is a transcription factor that controls the expression of a number of genes whose products mediate cell cycle arrest, DNA repair, senescence, or apoptosis. The critical role of p53 in prevention of carcinogenesis is supported by its universal inactivation in cancer cells either through mutations affecting the p53 locus directly or through aberration of its normal regulation. Because the DNA damage response pathway and the oncogenic stress pathway converge on p53, it has been thought that both pathways are integral to the tumor suppressor function of p53. Recent genetic studies, however, have provided compelling evidence indicating that the oncogenic stress pathway, rather than the DNA damage pathway, is essential for p53-mediated tumor suppression. Using a genetically engineered mouse model in which p53 status can be reversibly switched in vivo between functional and inactive states, it has been shown that the p53-mediated DNA damage responses are irrelevant to tumor suppression but are responsible for the pathological consequences. Of interest is the finding that delayed p53 restoration until the acute DNA damage response has subsided retains the protection against cancer development and such protection depends on p19ARF. Consistent with the notion that the acute DNA damage response may be dispensable for p53-mediated tumor suppression is a mouse genetic study in which endogenous p53 was replaced by a mutant that cannot be phosphorylated by DNA damage-activated protein kinases (ATM, ATR or Chk2). The knockin mice were incompetent for DNA damage-induced apoptosis yet fully protected from cancer development. These studies together indicate that temporary suppression of p53 activity can significantly reduce DNA damage-induced cytotoxicity without compromising the tumor suppression function, providing a rationale to explore temporary p53 inhibition as an approach of cancer therapy protection.

Arsenic is a naturally occurring metalloid that induces oxidative stress by activating NADPH oxidase activity through a Ras-GTPase-dependent mechanism, which creates an intracellular burst of reactive oxygen. Exposure of human, experimental animals and cultured cells to arsenic is associated with a variety of diverse effects. While arsenic is an established human carcinogen, there has been much controversy about the shape of the arsenic response curve, particularly at low doses. This controversy is further complicated by the fact that the mechanism of arsenic carcinogenesis remains unclear because of a lack of consistent success in inducing cancer in animal models through arsenic exposure. Epidemiological studies that include low dose data also indicate that exposure to arsenic in drinking water at concentrations of less than approximately 60 ppb (0.8 µM) is associated with risks of bladder or lung cancer that are below control values. However, when absorbed at toxic levels, arsenic causes severe health problems, including cancer. For instance, in many regions of Bangladesh, high concentrations of arsenic in drinking water becomes a particular health concern as it has been correlated with increased cancer rates. But arsenic has also been touted as having beneficial effects on health at lower doses. For instance, from the 18th to early 20th century, an inorganic arsenic preparation known as Fowler's Solution (1% potassium arsenate) was used in the treatment of a variety of diseases including skin cancers, hypertension, and arthritis. Arsenic was even applied to the skin by women to improve their complexion. A concentration-related hierarchy of responses to arsenic has been well documented. For example, in human adult foreskin keratinocytes, arsenite treatment at concentrations at or below 5 µM for 24 hr resulted in induced proliferation that is accompanied with enhanced nuclear factor-κB (NF-κB) and activator protein-1 (AP-1) activity, transcription factors that are known to promote cell proliferation and cell survival. At concentrations of 10 µM or greater, a statistically significant decrease of cell viability was observed. In support of the distinct nature of the cellular effects induced by low and high concentrations of arsenic, a genomic analysis showed that low dose (5 µM, non-cytotoxic) and high dose (50 µM, cytotoxic) affected expression of almost completely non-overlapping subsets of genes, consistent with a qualitative switch from a pro-survival biological response at low doses to a pro-death response at high doses. Together, the available information indicates a biphasic dose response of arsenic; the effects induced by low-dose arsenic are not only different in magnitude from that of high-dose arsenic but also in nature, i.e. cytoprotective versus cytotoxic.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Low-Doses of Arsenic Suppress p53 Activity by Inducing its Cytoplasmic Distribution.

Brief treatment of cells with sodium arsenite at low-doses (1-10 µM for 12 h) is associated with upregulation of Hdm2 and accumulation of p53 in the cytoplasm. Through the MAPK pathway, low-levels of arsenite stimulate the P2 promoter-mediated expression of Hdm2, which then promotes p53 ubiquitination and subsequent nuclear export. As a consequence, the p53 response to genotoxic stress is compromised, as evidenced by the impaired p53 activation and apoptosis in response to UV irradiation or 5FU treatment. The ability of arsenite to impede p53 activation is further demonstrated by a significantly blunted p53-dependent tissue damages induced by 5FU treatment when mice were fed with arsenite-containing water.

Pretreatment of Tumor-Bearing Mice with Low-Doses of Arsenic Protects Normal Tissues but Not Cancer Cells from Chemotherapy and Irradiation-Induced Killing In an experiment, lung carcinoma cell line A549 was used to generate a mouse xenograft model for assessing the effect of arsenic. Athymic nude mice (Balb c nu/nu, 4-6 weeks old) were purchased from Harlan laboratories. Mice were housed under pathogen-free conditions and maintained on a 12 h light/12 h dark cycle, with food and water supplied ad libitum. Human lung carcinoma cells A549 (cells as a 50% suspension in matrigel) as 3 million cells per mice in a final volume of 100 µl were injected subcutaneously in the right flank of Balb c nude mice. When the average tumor volume reached about 100 mm³, mice were randomized into the following groups; control; arsenite only; 5FU only; arsenite and 5FU; X-ray irradiation only; arsenite and X-ray irradiation. For arsenite pretreatment, mice were fed with water containing sodium arsenite (as 1.0 mg/L) for 3 days. Mice were then treated with either 5FU (30 mg/kg body weight) intravenously or irradiated with 2Gy total body irradiation ("TBI") daily for one week. Tumor volumes were measured periodically. Tumor volume was calculated using the equation: (volume=length× width×depth×0.5236 mm³). Body weight was also monitored throughout the period of the experiment. The numbers are means±SE from two independent experiments with total of 10 mice per group.

Figure 2:
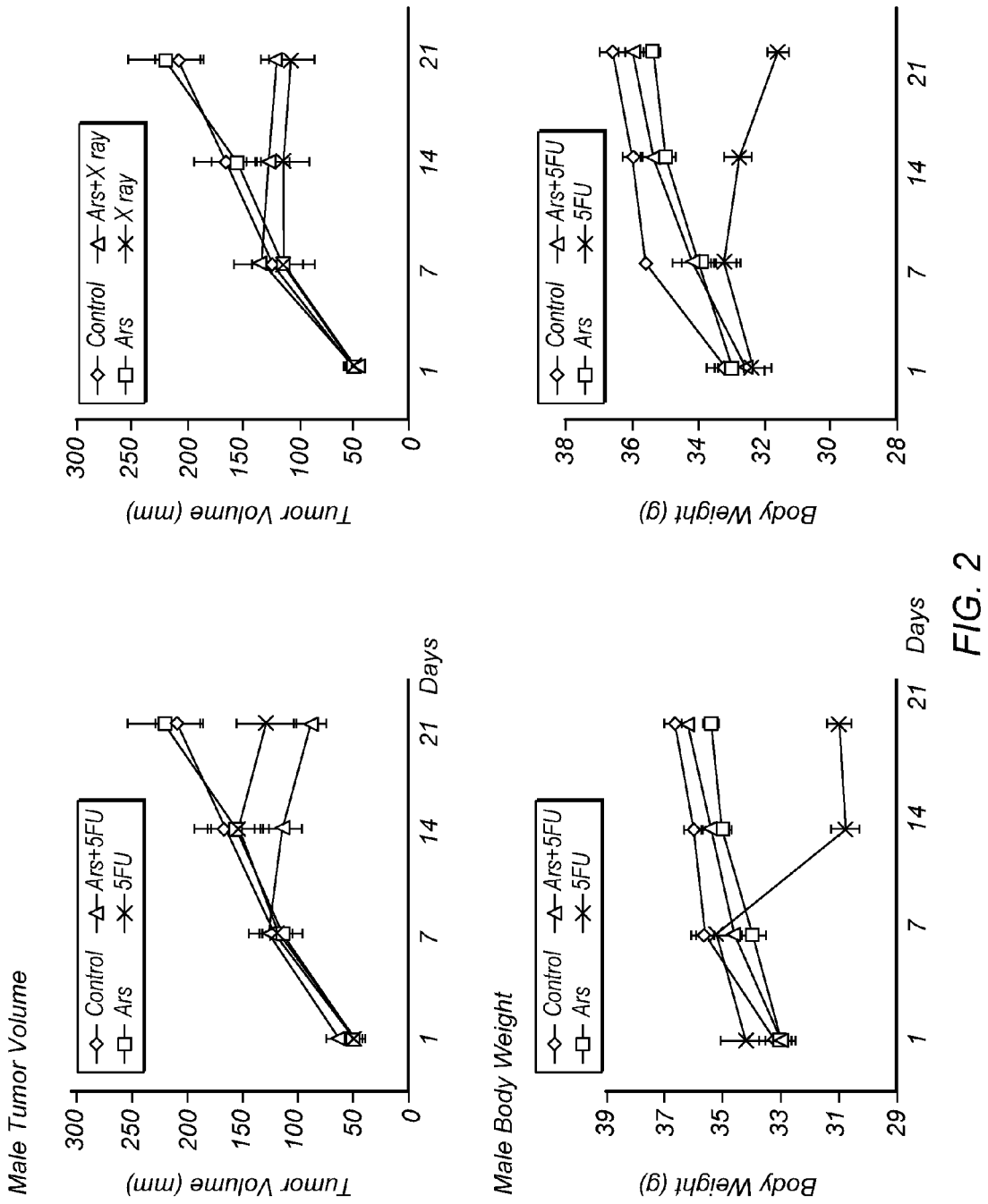
FIG. 2 depicts the effect of arsenic pretreatment on female mice injected with human lung carcinoma cells under various treatment conditions.

In the vehicle or control group, the tumor volume continued to increase with time (See FIGS. 1 and 2). Arsenic treatment did not have any detectable effect on growth of the implant tumors, indicating that such a short arsenic treatment causes neither promotion nor inhibition of tumor progression. As expected, treatment with either 5FU (30 mg/kg body weight) via intravenous treatment or irradiation at 2Gy as total body irradiation (TBI) daily for one week resulted in marked tumor regression. Significantly, arsenic pretreatment showed little effect on both 5FU and irradiation-induced tumor suppression, as evidenced by the observation that 5FU or irradiation-induced tumor regression is indistinguishable between the two groups that were pretreated with or without sodium arsenite (FIGS. 1 and 2). Our data thus indicates that low-dose arsenic pretreatment does not detectably affect the efficacy of 5FU and radiation, at least in the human lung carcinoma xenograft mouse model.

To test whether low-dose arsenic could protect normal tissues from damages caused by 5FU or irradiation in these tumor-bearing mice, we monitored body weight change throughout the experimental period. Body weight of the mice treated as described in the experiment was monitored throughout the period of the experiment.

As shown in FIGS. 1 and 2, the body weight of control mice did not level off until week 7 and increased slightly afterwards. Interestingly, arsenic-treated mice showed little loss of body weight. In a sharp contrast, mice treated with either 5FU or irradiation significantly lost their body weight. This is likely caused by toxicity of the treatments as tumor growth in those animals was almost completely suppressed (see FIGS. 1 and 2). Significantly, such therapy-induced body weight loss was effectively prevented by arsenic pretreatment, as demonstrated by a minimum decrease in body weight of the mice fed with arsenic-containing water.

To assess the effect of arsenic at the tissue level, we examined the small intestine and bone marrow cells, two tissues most sensitive to chemotherapy and radiation treatment. Consistent with the observations at the whole animal level, 5FU and radiation treatments were associated with severe damages to small intestine and bone marrow cells, and such damages were significantly inhibited by low-dose arsenic pretreatment. Collectively, the results demonstrate that a brief treatment with low-dose arsenic is associated with a marked protection of normal tissues without compromising the ability of 5FU and irradiation to kill carcinoma cells.

Duration of Arsenic Pretreatment to Provide Maximal Protection

We next determined the duration of arsenic pretreatment that could provide maximal protection. We pretreated tumor-bearing mice with 1.0 mg/L of arsenic in the drinking water for 1, 2, 3, 4, 5, 6, or 7 days. The animals were again treated with 5FU (30 mg/kg body weight) daily for one week and body weight change was monitored. The results indicate that while 1 and 2 days arsenic pretreatment resulted in a protection less than 3-day pretreatment, there was no further increase of benefits from pretreatments longer than 3-day. Together, out data indicates that 3-day arsenic pretreatment appears to be adequate for an optimal protection.

Arsenic-Mediated p53 Inhibition is Temporary and Reversible

Recognizing the potential cancer risk associated with arsenic, we examined whether the low-dose arsenic-mediated p53 inhibition is reversible. After culturing in media containing 5 µM sodium arsenite for 3 days, MCF10A cells, a non-transformed human breast epithelial cell line, were recovered in arsenic-free media for 1, 3, 5, 7, 9, or 11 days and assessed for the p53 response to irradiation. Radiation-induced p53 activation, was reflected by induction of the p53 protein abundance and p21 expression, and was not detectable until cells had been cultured in arsenic-free media for 5 days and was almost completely recovered 7 days after arsenic removal. Consistent with the Western result, immuno-staining revealed a nuclear redistribution of p53 in cells that had been cultured in arsenic-free media for 5 days. Together, the results with cultured cells indicate that the arsenic-mediated p53 inhibition is transient and can be completely reversed once arsenic treatment is discontinued.

We next used mice to examine arsenic-mediated modulation of p53 activity in vivo. To this end, we used peripheral blood lymphocytes to monitor the p53 response to irradiation. Mice were fed with water containing sodium arsenite for 3 days. Whole blood was collected from the animals 1, 3, 5, 7, 9, or 11 days after arsenic removal. Lymphocytes were isolated by using the Ficoll method. The cells were cultured for 24 h, then irradiated at a dose of 2 Gy and harvested 3 hours post-treatment. Western analysis was performed. Consistent with the results from cell-based studies, p53 activation by radiation recovered, albeit with a slightly slower kinetics, after arsenic was removed. Radiation-induced p53 accumulation and p21 expression were suppressed at 0 and 1 day post-irradiation, partially recovered at day 7 and completely back to the untreated level at day 9. Collectively, our data indicate that low-dose arsenic-induced p53 suppression is temporary and reversible.

Human Breast MDA MB-231 Xenograft Female Mice

Athymic nude mice (Balb c nu/nu, 4-6 weeks old) were purchased from Harlan laboratories. Mice were housed under pathogen-free conditions and maintained on a 12 h light/12 h dark cycle, with food and water supplied ad libitum. Human breast carcinoma cells, MDA-MB-231 (cells as a 50% suspension in matrigel) as 3 million cells per mice in a final volume of 100 ml were injected subcutaneously at right flank of Balb c nude mice. When the average tumor volume reached about 100 mm$^3$, mice were randomized into following groups; control; 5FU only; arsenite and 5FU. For arsenite pretreatment, mice were fed with water containing sodium arsenite (as 1.0 mg/L) for 3 days or underwent intraperitoneal ('IP") pretreatment (10 µg/day for 3 days). Mice were then treated with 5FU (30 mg/kg body weight) via an i.v. daily for one week. Tumor volumes were measured periodically. Tumor volume was calculated using the equation: (volume=length×width×depth×0.5236 mm3). Body weight was monitored throughout the period of the experiment. The numbers are means±SE from two independent experiments with total of 10 mice per group. Results from this experiment are presented in FIG. 3.

Figure 3:
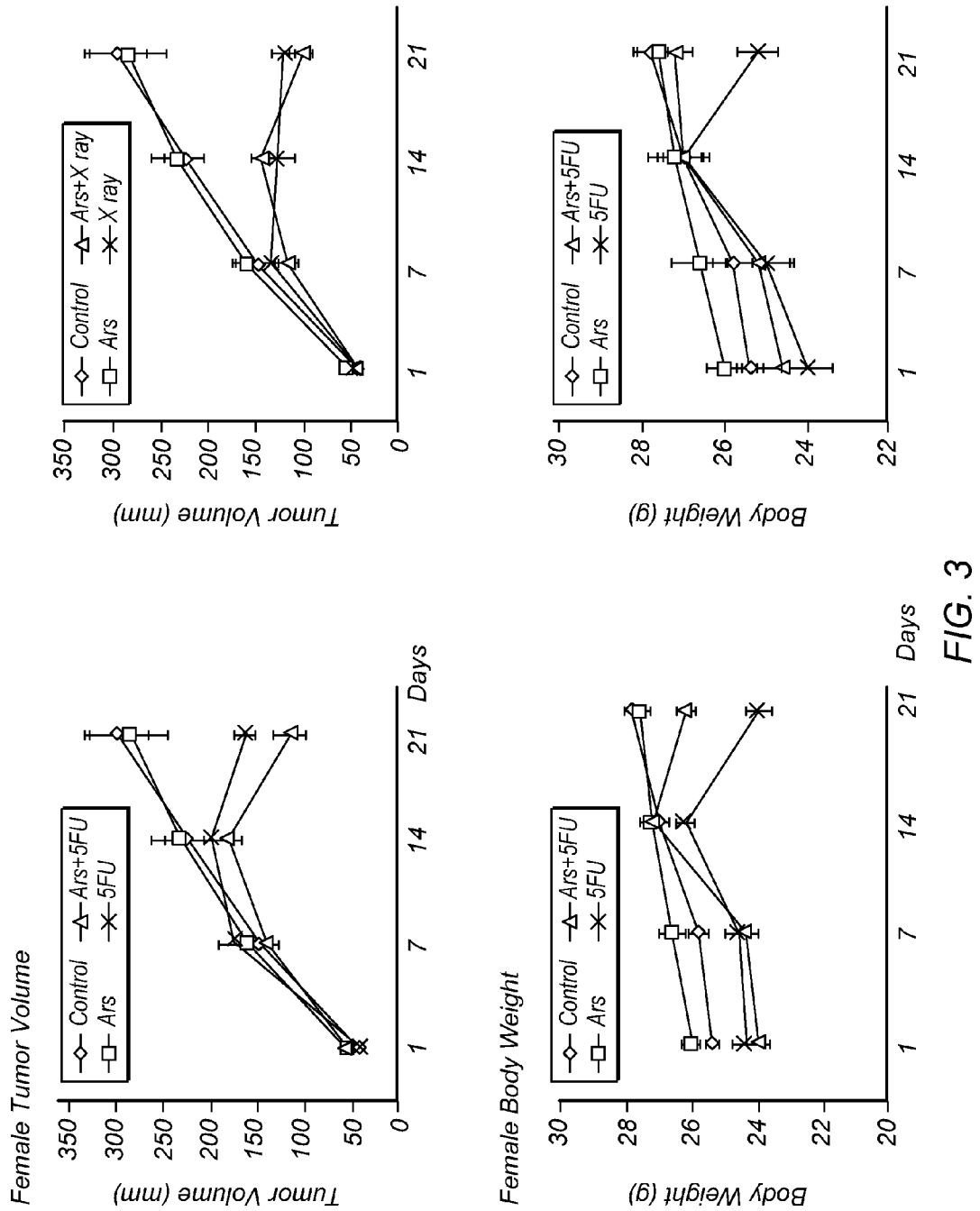
FIG. 3 depicts the effect of arsenic pretreatment on mice injected with human breast carcinoma cells under various treatment conditions.

As expected, the tumor volume in the vehicle or control group continued increase with time (FIG. 3). Treatment with 5FU (30 mg/kg body weight i.v.) daily for one week resulted in marked tumor regression. Arsenic pretreatment showed little effect on 5FU-induced tumor suppression, as evidenced by the observation that 5FU-induced tumor regression is indistinguishable between the two groups that were pretreated with or without sodium arsenite (FIG. 3). To examine whether low-dose arsenic could protect normal tissues from damages caused by 5FU in these tumor-bearing mice, we monitored body weight change throughout the experimental period. In a sharp contrast to control mice, that showed little loss of body weight, mice treated with 5FU exhibited a significant decrease in body weight. 5FU-induced body weight loss was almost completely prevented by arsenic pretreatment, as demonstrated by a minimum decrease in body weight of mice that were pre-treated with sodium arsenite.

Human Colon carcinoma Xenograft (5FU)

Athymic nude mice (Balb c nu/nu, 4-6 weeks old) were purchased from Harlan laboratories. Mice were housed under pathogen-free conditions and maintained on a 12 h light/12 h dark cycle, with food and water supplied ad libitum. Human colon carcinoma cells, SW-480 (cells as a 50% suspension in matrigel) as 3 million cells per mice in a final volume of 100 ml were injected subcutaneously at right flank of Balb c nude mice. When the average tumor volume reached about 100 mm$^3$, mice were randomized into following groups; control; arsenite, 5FU only; arsenite and 5FU. For arsenite pretreatment, mice were fed with water containing sodium arsenite (as 1.0 mg/L) for 3 days. Mice were then treated with 5FU (30 mg/kg body weight) via an i.v. daily for one week. Tumor volumes were measured periodically. Tumor volume was calculated using the equation: (volume=length×width×depth×0.5236 mm3). Body weight was monitored throughout the period of the experiment. The numbers are means±SE from two independent experiments with total of 10 mice per group. Results from this experiment are presented in FIG. 4.

Figure 4:
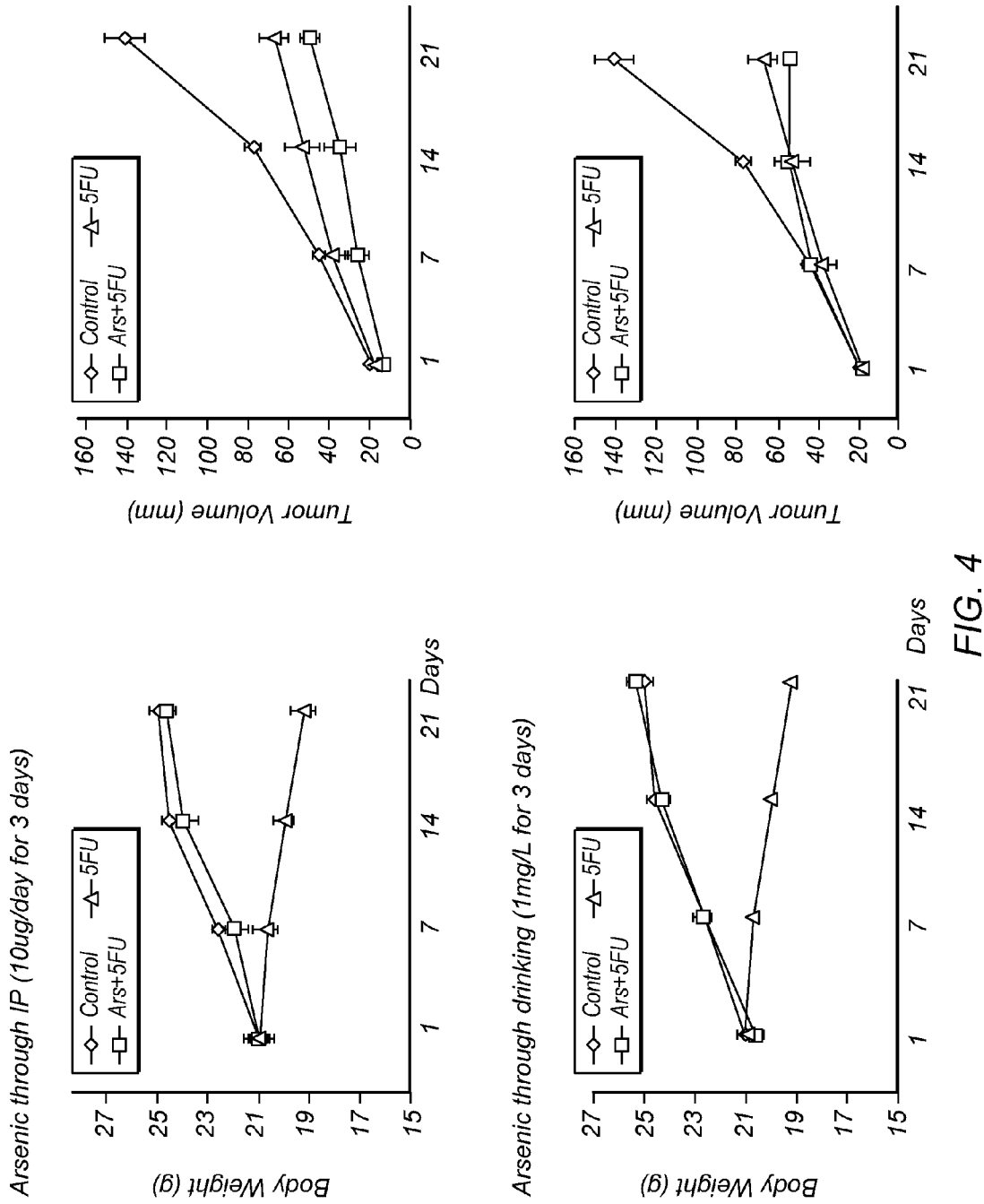
FIG. 4 depicts the effect of arsenic pretreatment on mice injected with human colon carcinoma cells under various treatment conditions.

As expected, the tumor volume in the vehicle or control group continued increase with time (FIG. 4). Arsenic treatment did not have any detectable effect on growth of the implanted tumors, indicating that such a brief treatment with a low dose arsenic caused neither promotion nor inhibition of tumor progression. Treatment with 5FU (30 mg/kg body weight i.v.) daily for one week resulted in marked tumor regression. Arsenic pretreatment showed little effect on 5FU-induced tumor suppression, as evidenced by the observation that 5FU-induced tumor regression is indistinguishable between the two groups that were pretreated with or without sodium arsenite. There was little difference between male and female mice in response to the treatment of 5FU and arsenic. Our data thus indicate that a short low-dose arsenic pretreatment does not detectably affect the efficacy of 5FU, at least in the human colon carcinoma xenograft mouse model.

To examine whether low-dose arsenic could protect normal tissues from damages caused by 5FU in these tumor-bearing mice, we monitored body weight change throughout the experimental period. In a sharp contrast to control and arsenic-treated mice that showed little loss of body weight, mice treated with 5FU exhibited a significant decrease in body weight. This is likely caused by toxicity of the treatments as tumor in those animals was almost completely regressed. Significantly, the 5FU-induced body weight loss was almost completely prevented by arsenic pretreatment, as demonstrated by a minimum decrease in body weight of both male and female mice that were fed with arsenic-containing water.

To corroborate the result of body weight measurement, we assessed the effect of arsenic at the tissue level by examining the small intestine and bone marrow cells, two tissues most sensitive to chemotherapeutics induced damage. Consistent with the observations with whole animals, 5FU treatments were associated with severe damages to the small intestine, as evidenced by marked alterations in both size and morphology of the small intestine crypts. Such damages were significantly ameliorated by low-dose arsenic pretreatment. The protective effect of arsenic is also evident in the bone marrow. Bone marrow cell exhaustion was clearly observed in 5FU-treated mice, however, this decrease of bone marrow cellularity was considerably alleviated in arsenic-pretreated mice. Collectively, the results demonstrate that a brief treatment with low-dose arsenic is associated with a marked protection of normal tissues without compromising the ability of 5FU to kill carcinoma cells.

C57BL/6 WT and R172P Knock-in Mice

Figure 5:
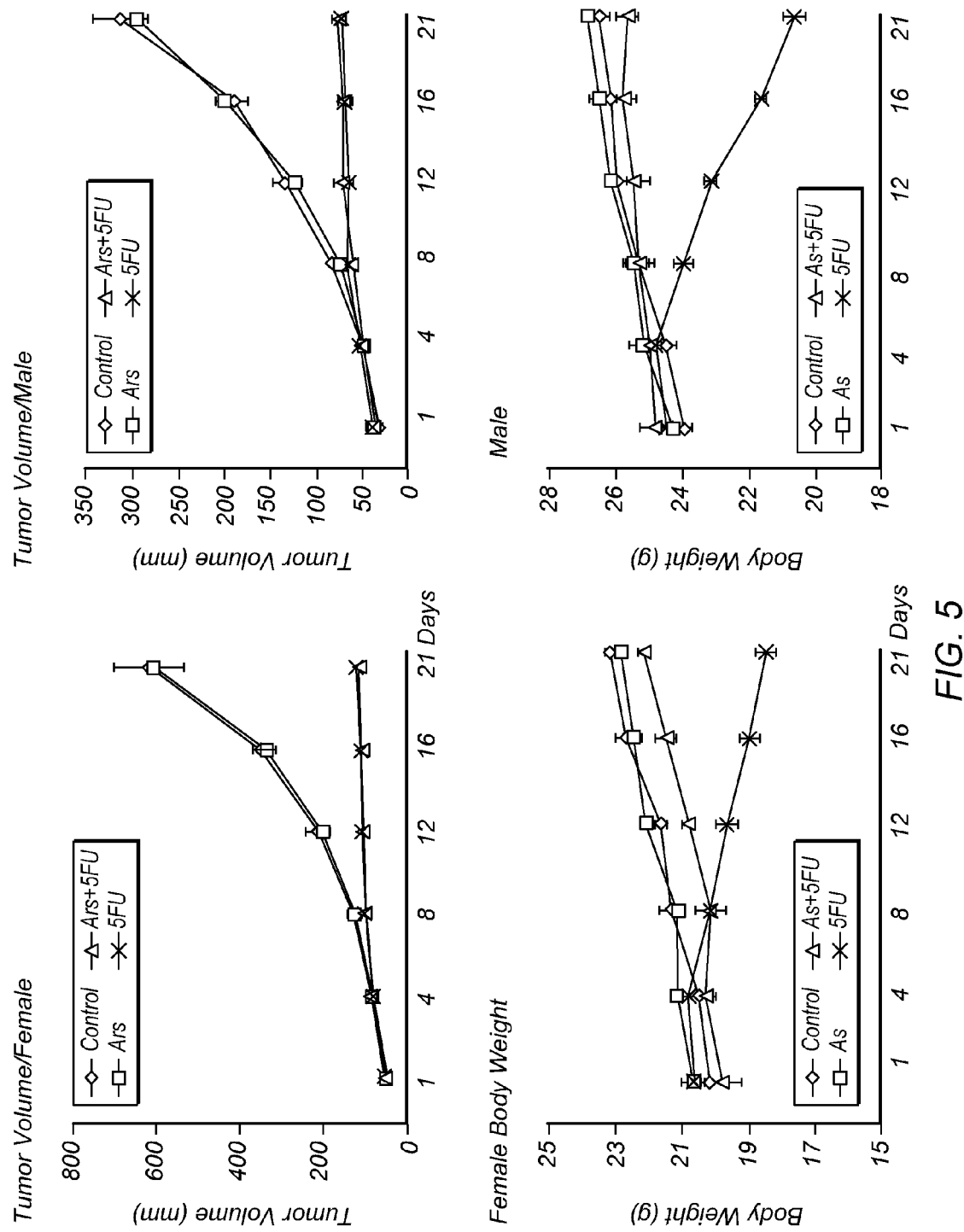
FIG. 5 depicts the effect of arsenic pretreatment on WT mice vs. p53 R172P knock in mice under x-ray irradiation.

Our prior work showed that the mechanism underlying low-dose arsenic-mediated suppression of apoptosis is inhibition of p53. Mutant p53 expressing mouse model was employed to test whether the observed protective effect of arsenic was mediated by p53 inactivation. Black C57BL/6 WT or p53 R172 knock in mice at age of 4-6 weeks old) were obtained from Dr. Lazona. Mice were housed under pathogen-free conditions and maintained on a 12 h light/12 h dark cycle, with food and water supplied ad libitum., mice were randomized into following groups; control; X-ray irradiation only; arsenite and X-ray irradiation. For arsenite pretreatment, mice were fed with water containing sodium arsenite (as 1.0 mg/L) for 3 days. Mice were then irradiated with 2Gy TBI daily for one week. Body weight was monitored throughout the period of the experiment. The numbers are means±SE from two independent experiments with total of 10 mice per group. Results from this experiment are presented in FIG. 5.

In contrast with the wild type littermates, arsenic provided little protection against 5FU-induced toxicity in p53 mutant mice, supporting the model in which arsenic exerts the protective effect selective to healthy normal tissues via suppression of p53.

SUMMARY

Not to be bound to any particular theory, it is believed that low-dose arsenic pretreatment can effectively protect normal tissues from DNA damage-induced pathological consequences via a mechanism of temporary p53 suppression. Of importance is the finding that the protection is selective to normal tissues and cancer cells do not share this protective response because of their defective p53. We also established a method of using peripheral lymphocytes to monitor the effect of arsenic on p53 activity.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of inhibiting damage to the small intestine in a human subject resulting from chemotherapeutic treatment of cancer cells in the human subject, comprising:
    a) administering to the subject arsenic and/or one or more compounds of arsenic in an amount from about 1 μg/kg/day to about 30 μg/kg/day; and
    b) administering to the subject a therapeutically effective amount of one or more chemotherapeutic agents that activate p53, from one to eight days after the administration of the arsenic and/or one or more compounds of arsenic,
wherein the arsenic and/or one or more compounds of arsenic supress p53 activity and inhibit damage to the small intestine in the human subject resulting from administration of the one or more chemotherapeutic agents to the human subject.

2. The method of claim 1, wherein the arsenic and/or one or more compounds of arsenic is administered to the human subject three to eight days prior to administering the one or more chemotherapeutic agents to the human subject.

3. A method of inhibiting damage to bone marrow cells in a human subject resulting from chemotherapeutic treatment of cancer cells in the human subject, comprising:
    a) administering to the subject arsenic and/or one or more compounds of arsenic in an amount from about 1 μg/kg/day to about 30 μg/kg/day; and
    b) administering to the subject a therapeutically effective amount of one or more chemotherapeutic agents that activate p53, from one to eight days after the administration of the arsenic and/or one or more compounds of arsenic,
wherein the arsenic and/or one or more compounds of arsenic suppress p53 activity and inhibit damage to the bone marrow cells in the human subject resulting from administration of the one or more chemotherapeutic agents to the human subject.

4. The method of claim 3, wherein the arsenic and/or one or more compounds of arsenic are administered to the human subject three to eight days prior to administering the one or more chemotherapeutic agents to the human subject.

5. A method of inhibiting damage to the small intestine in a human subject resulting from radiation treatment of cancer cells in the human subject, comprising:
    a) administering to the subject arsenic and/or one or more compounds of arsenic in an amount from about 1 μg/kg/day to about 30 μg/kg/day; and
    b) administering to the subject a therapeutically effective amount of radiation that activates p53, from one to eight days after the administration of the arsenic and/or one or more compounds of arsenic, wherein the arsenic and/or one or more compounds of arsenic suppress p53 activity and inhibit damage to the small intestine in the human subject resulting from administration of the radiation to the human subject.

6. The method of claim 5, wherein the arsenic and/or one or more compounds of arsenic is administered to the human subject three to eight days prior to administering the radiation to the human subject.

7. A method of inhibiting damage to bone marrow cells in a human subject resulting from radiation treatment of cancer cells in the human subject, comprising:
   a) administering to the subject arsenic and/or one or more compounds of arsenic to the subject in an amount from about 1 µg/kg/day to about 30 µg/kg/day; and
   b) administering to the subject a therapeutically effective amount of radiation that activates p53, from one to eight days after the administration of the administration of the arsenic and/or one or more compounds of arsenic,
wherein the arsenic and/or one or more compounds of arsenic suppress p53 activity and inhibit damage to the bone marrow cells in the human subject resulting from administration of the radiation to the human subject.

8. The method of claim 7, wherein the arsenic and/or one or more compounds of arsenic are administered to the human subject three to eight days prior to administering the radiation to the human subject.

* * * * *

UNITED STATES PATENT AND TRADEMARK OFFICE
CERTIFICATE OF CORRECTION

PATENT NO. : 8,795,738 B2
APPLICATION NO. : 12/945430
DATED : August 5, 2014
INVENTOR(S) : Yuan et al.

It is certified that error appears in the above-identified patent and that said Letters Patent is hereby corrected as shown below:

Title Page, Item (75) Inventor, should read

--(75) Inventors: Zhi-Min Yuan, San Antonio, TX (US); Chul Soo Ha, Houston, TX (US)--.

Signed and Sealed this
Twenty-fourth Day of May, 2016

Michelle K. Lee
*Director of the United States Patent and Trademark Office*